United States Patent
Hendriks et al.

(10) Patent No.: US 12,245,821 B2
(45) Date of Patent: Mar. 11, 2025

(54) ENDOTRACHEAL TUBE SIZE SELECTION AND INSERTION DEPTH ESTIMATION USING STATISTICAL SHAPE MODELLING AND VIRTUAL FITTING

(71) Applicant: KONINKLIJKE PHILIPS N.V., Eindhoven (NL)

(72) Inventors: Cornelis Petrus Hendriks, Eindhoven (NL); Kiran Hamilton J. Dellimore, Eindhoven (NL); Joerg Sabczynski, Hamburg (DE); Thomas Koehler, Hamburg (DE); Jaap Roger Haartsen, Eindhoven (NL); Rafael Wiemker, Hamburg (DE); Michael Polkey, London (GB)

(73) Assignee: Koninklijke Philips N.V., Eindhoven (NL)

( * ) Notice: Subject to any disclaimer, the term of this patent is extended or adjusted under 35 U.S.C. 154(b) by 421 days.

(21) Appl. No.: 17/737,421

(22) Filed: May 5, 2022

(65) Prior Publication Data
US 2023/0009274 A1  Jan. 12, 2023

Related U.S. Application Data
(60) Provisional application No. 63/219,370, filed on Jul. 8, 2021.

(51) Int. Cl.
*A61B 34/10* (2016.01)
*A61B 6/03* (2006.01)
*G06T 7/62* (2017.01)

(52) U.S. Cl.
CPC ............. *A61B 34/10* (2016.02); *A61B 6/032* (2013.01); *G06T 7/62* (2017.01); *A61B 2034/102* (2016.02); *A61B 2034/105* (2016.02)

(58) Field of Classification Search
CPC ... A61B 34/10; A61B 6/032; A61B 2034/102; A61B 2034/105; A61B 5/082;
(Continued)

(56) References Cited

U.S. PATENT DOCUMENTS

| 2004/0097805 A1* | 5/2004 | Verard | A61B 34/20 600/428 |
| 2010/0081916 A1* | 4/2010 | Hyde | A61B 5/4839 600/407 |

(Continued)

OTHER PUBLICATIONS

Shim JG, Ryu KH, Lee SH, Cho EA, Lee S, Ahn JH. Machine learning model for predicting the optimal depth of tracheal tube insertion in pediatric patients: A retrospective cohort study. PLoS One. Sep. 2, 2021;16(9):e0257069. (Year: 2021).*

(Continued)

*Primary Examiner* — Fayyaz Alam
(74) *Attorney, Agent, or Firm* — Daniel H. Brean (57) ABSTRACT

An intubation assistance device includes an electronic controller configured to: generate a patient respiratory tract geometry model of at least a portion of a human respiratory tract by inputting one or more patient variables into a statistical shape model (SSM) of at least a portion of the human respiratory tract; select a recommended endotracheal tube (ETT) size by modeling at least one ETT model inserted into the patient respiratory tract geometry model to form a virtual fit model and estimating at least one fit parameter based on the virtual fit model; and display the recommended ETT size on a display device.

16 Claims, 3 Drawing Sheets

(58) Field of Classification Search
CPC ....... A61B 5/1077; A61B 5/055; A61B 5/087; A61B 5/1076; G06T 7/62; G06T 2207/20084; G16H 20/40; G16H 40/63; G16H 50/50
See application file for complete search history.

(56) References Cited

U.S. PATENT DOCUMENTS

| | | | |
|---|---|---|---|
| 2011/0263935 A1* | 10/2011 | Qiu | G06F 18/2415 382/128 |
| 2022/0171890 A1 | 6/2022 | Bergounioux | |
| 2022/0202497 A1* | 6/2022 | Janna | A61B 17/1764 |
| 2023/0200629 A1* | 6/2023 | Yang | B25J 9/1689 700/245 |

OTHER PUBLICATIONS

Xiao X, Zhao S, Zhang X, Soghier L, Hahn J. Automated assessment of neonatal endotracheal intubation measured by a virtual reality simulation system. In2020 42nd Annual International Conference of the IEEE Engineering in Medicine & Biology Society (EMBC) Jul. 2, 20200 (pp. 2429-2433). IEEE. (Year: 2020).*

Zhao S, Xiao X, Wang Q, Zhang X, Li W, Soghier L, Hahn J. An intelligent augmented reality training framework for neonatal endotracheal intubation. In2020 IEEE International Symposium on Mixed and Augmented Reality (ISMAR) Nov. 9, 2020 (pp. 672-681). IEEE. (Year: 2020).*

Epstein, S.K., "Narrow" Thinking About Difficult Weaning: Don't Forget the Endotracheal Tube, Respiratory Care, Dec. 2012, vol. 57, No. 12.

O'callaghan, D. et al., "What size tube doctor? Bigger may be better—at least for weaning." Critical Care 2013, 17:422.

Endotracheal Tube, Family Practice Notebook, https://fpnotebook.com/Lung/Procedure/EndtrchlTb.htm.

Endotracheal Tube Size Calculator, Omni Calculator, https://www.omnicalculator.com/health/ett-size#et-tube-size-formula.

Use ultrasound for confirmation of endotracheal tube intubation!, SinaiEM, https://sinaiem.org/foam/use-ultrasound-for-confirmation-of-endotracheal-tube-intubation/.

Evaluation of endotracheal tube position, Radiopaedia, https://radiopaedia.org/articles/evaluation-of-endotracheal-tube-position?lang=us.

Ambellan, F. et al., 2019, "Statistical Shape Models: Understanding and Mastering Variation in Anatomy". In: Rea P. (eds) Biomedical Visualisation. Advances in Experimental Medicine and Biology, vol. 1156. Springer, Cham. https://doi.org/10.1007/978-3-030-19385-0_5. Abstract.

Humphries, S.M. et al. 2016, "Analysis of pediatric airway morphology using statistical shape modelling", Med Biol Eng Comput (2016) 54:899-911.

Zwirner, J, et al., 2020, "Load-deformation characteristics of acellular human scalp: assessing tissue grafts from a material testing perspective". Sci Rep. Nov. 6, 2020;10(1):19243. doi: 10.1038/s41598-020-75875-z. PMID: 33159106; PMCID: PMC7648071.

International Search Report for PCT/EP2022/067859 filed Jun. 29, 2022.

Pinho, R. et al., "Tracheal stent prediction using statistical deformable models of tubular shapes", Spie Smart Structure and Materials + Nondestructive Evaluation and Health Monitoring, (2008), vol. 6914, p. 691440.

De Kleijn, B. et al. "Virtual 3D planning of tracheostomy placement and clinical applicability of 3D cannula design: a three-step study", European Archives of Oto-Rhino-Laryngology, Springer Berlin Heidelberg, vol. 275, No. 2, (2017), pp. 451-457.

* cited by examiner

ENDOTRACHEAL TUBE SIZE SELECTION AND INSERTION DEPTH ESTIMATION USING STATISTICAL SHAPE MODELLING AND VIRTUAL FITTING

CROSS-REFERENCE TO RELATED APPLICATIONS

This patent application claims the priority benefit under 35 U.S.C. § 119(e) of U.S. Provisional Application No. 63/219,370, filed on Jul. 8, 2021, the contents of which are herein incorporated by reference.

The following relates generally to the respiratory therapy arts, tracheal intubation arts, endotracheal tube sizing arts, and related arts.

BACKGROUND

Mechanical ventilation of a patient typically entails placement of an endotracheal tube (ETT) into a trachea of the patient, in a process known as tracheal intubation. The desired position of the tip of an ETT is approximately 5.0 cm (±2.0 cm) above a carina (i.e., a location where the trachea splits into the main right and left bronchus). Tracheal intubation is usually performed by an anesthesiologist or other qualified medical professional, and in a common sequence the head is moved backward to access the airway, and a laryngoscope is used to facilitate proper placement of the ETT between the vocal cords and into the trachea, without misplacement into the esophagus.

Common situations where mechanical ventilation is required can include intensive care unit (ICU) cases and during major surgery. Such patients often have images (e.g., computed tomography (CT) images) obtained of the thorax before being sent to the ICU, in particular if the patient's condition is a lung-related disease (e.g., Covid-19), or trauma.

However, the ETT may be incorrectly positioned (such as in the esophagus or one of the bronchi), or there is an air-leak in the ETT. Although uncommon, when these situations occur, it may lead to severe complications with long term consequences due to cerebral hypoxia.

An important consideration when intubating a patient is proper selection of the ETT size. ETTs are available in various sizes, e.g., from 2 mm to 10.5 mm internal diameter in some sizing schemes, with the smallest sizes being used for intubating infants. For patients older than one year, one formula for selecting the internal diameter in millimeters is $$\frac{Age + 16}{4}.$$

In addition to selecting ETT diameter, the depth of insertion of the ETT is another important sizing parameter. The end of the ETT is preferably positioned above the carina, that is, where the trachea branches into the left and right bronchial tubes leading into the respective lungs, in order to ensure a well-sealed fit while ventilating both the left and right lungs equally. The ETT usually has marks along its length (e.g., tic marks every 1 cm or the like) so that the tube insertion depth can be tracked visually during the tracheal intubation process. A formula for selecting the depth of insertion in centimeters is $$\frac{Age + 12}{2}.$$

While these are general rules, patient-specific anatomy can significantly impact ETT sizing (optimal tube diameter and depth of insertion), as well as the difficulty in performing the tracheal intubation.

Improper tracheal intubation can lead to serious complications, such as perforation of the trachea (or of the esophagus if the ETT is misplaced), nerve damage, spinal damage, vocal cord damage, inadequate mechanical ventilation via the inserted ETT, bronchial intubation (insertion of the ETT too deeply so that it enters the left or right bronchial tube), accidental dislodgment of the ETT, and so forth. Performing the tracheal intubation with a tube of the wrong size can directly or indirectly lead to many such complications. Intubation with an ETT of too-small diameter can lead to inadequate ventilation and possible dislodgement; whereas, using a too-large diameter can lead to excessive force being applied to the airway potentially leading to damage to nerves, vocal cords, or other airway tissue. Similarly, insufficient depth of insertion can lead to inadequate ventilation and possible dislodgment; whereas excessive depth of insertion can lead to bronchial intubation. The laryngoscope permits visual observation only of the upper airway structures (glottis and larynx), so that tracheal intubation is a partially "blind" procedure.

The following discloses certain improvements to overcome these problems and others.

SUMMARY

In one aspect, an intubation assistance device includes an electronic controller configured to: generate a patient respiratory tract geometry model of at least a portion of a human respiratory tract by inputting one or more patient variables into a statistical shape model (SSM) of at least a portion of the human respiratory tract; select a recommended endotracheal tube (ETT) size by modeling at least one ETT model inserted into the patient respiratory tract geometry model to form a virtual fit model and estimating at least one fit parameter based on the virtual fit model; and display the recommended ETT size on a display device.

In another aspect, an intubation assistance method includes, with an electronic controller: generating a patient respiratory tract geometry model of at least a portion of a human respiratory tract; selecting a recommended ETT size based on the patient respiratory tract geometry model and an estimation of at least one fit parameter; and displaying the recommended ETT size on a display device.

One advantage resides in providing mechanical ventilation therapy to a patient with an ETT of suitable diameter sizing inserted into the patient's trachea.

Another advantage resides in providing mechanical ventilation therapy to a patient with an ETT of suitable insertion depth sizing into the patient's trachea.

Another advantage resides in determining a suitable size of the ETT that takes into account the individualized anatomy of the patient.

Another advantage resides in determining a suitable ETT size for a patient based on one or more images of the patient.

Another advantage resides in using one or more models of the ETT and/or a patient geometry of the patient to determine a suitable size of the ETT.

Another advantage resides in using one or more models of the ETT and/or a patient geometry of the patient to determine an insertion depth of the ETT into the patient's trachea.

Another advantage resides in using a statistical shape model (SSM) to determine a suitable size of the ETT and/or a suitable insertion depth for the ETT.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

As used herein, the singular form of "a", "an", and "the" include plural references unless the context clearly dictates otherwise. As used herein, statements that two or more parts or components are "coupled," "connected," or "engaged" shall mean that the parts are joined, operate, or co-act together either directly or indirectly, i.e., through one or more intermediate parts or components, so long as a link occurs. Directional phrases used herein, such as, for example and without limitation, top, bottom, left, right, upper, lower, front, back, and derivatives thereof, relate to the orientation of the elements shown in the drawings and are not limiting upon the scope of the claimed invention unless expressly recited therein. The word "comprising" or "including" does not exclude the presence of elements or steps other than those described herein and/or listed in a claim. In a device comprised of several means, several of these means may be embodied by one and the same item of hardware.

Figure 1:
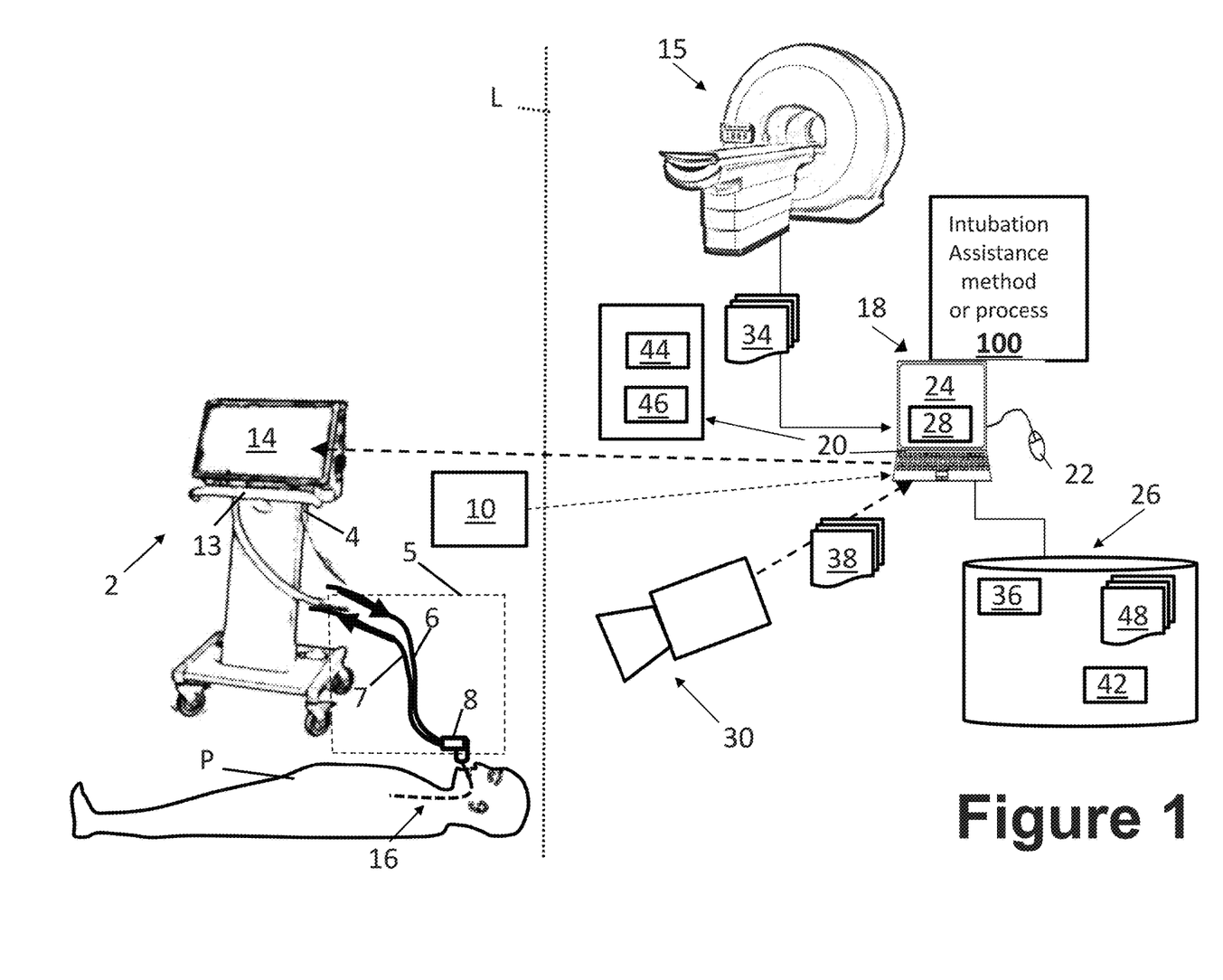
FIG. 1 diagrammatically shows an illustrative mechanical ventilation system including an intubation assistance device in accordance with the present disclosure.

With reference to FIG. 1, a mechanical ventilator 2 for providing ventilation therapy to an associated patient P is shown. As shown in FIG. 1, the mechanical ventilator 2 includes an outlet 4 connectable with a patient breathing circuit 5 to delivery mechanical ventilation to the patient P. The patient breathing circuit 5 includes typical components for a mechanical ventilator, such as an inlet line 6, an optional outlet line 7 (this may be omitted if the ventilator employs a single-limb patient circuit), a connector or port 8 for connecting with an ETT, and one or more breathing sensors (not shown), such as a gas flow meter, a pressure sensor, end-tidal carbon dioxide (etCO$_2$) sensor, and/or so forth. The mechanical ventilator 2 is designed to deliver air, an air-oxygen mixture, or other breathable gas (supply not shown) to the outlet 4 at a programmed pressure and/or flow rate to ventilate the patient via an ETT.

FIG. 1 also shows a medical imaging device 15 (also referred to as an image acquisition device, imaging device, and so forth). The image acquisition device 15 can be a Computed Tomography (CT) image acquisition device, a C-arm imager, or other X-ray imaging device; Magnetic Resonance (MR) image acquisition device; an ultrasound (US) image acquisition device; or a medical imaging device of another modality. As primarily described herein, the medical imaging device 15 comprises a CT medical imaging device 15. As described herein, the medical imaging device 15 is used to acquire images of the patient P based upon which ETT sizing is performed. It should be noted that the imaging device 15 may not be located in the same room, or even the same department, as the mechanical ventilator 2. For example, the medical imaging device 15 may be located in a radiology laboratory while the mechanical ventilator 2 may be located in an intensive care unit (ICU), cardiac care unit (CCU), in a hospital room assigned to the patient P, or so forth. This is diagrammatically indicated in FIG. 1 by separator line L.

FIG. 1 diagrammatically illustrates the patient P intubated with an endotracheal tube (ETT) 16 (the lower portion of which is inside the patient P and hence is shown in phantom). The connector or port 8 connects with the ETT 16 to operatively connect the mechanical ventilator 2 to deliver breathable air to the patient P via the ETT 16. The mechanical ventilation provided by the mechanical ventilator 2 via the ETT 16 may be therapeutic for a wide range of conditions, such as various types of pulmonary conditions like emphysema or pneumonia, viral or bacterial infections impacting respiration such as a COVID-19 infection or severe influenza, cardiovascular conditions in which the patient P receives breathable gas enriched with oxygen, or so forth.

FIG. 1 shows the patient P already intubated. That is, FIG. 1 shows the patient after a tracheal intubation has been performed to insert the ETT 16 into the patient. However, to safely perform the tracheal intubation, the anesthesiologist or other qualified medical professional first performs an assessment of the patient P to select the ETT size of the ETT 16, and then inserts an ETT of the selected size into the patient P by a tracheal intubation procedure.

As a further note, as used herein the "ETT size" includes an ETT diameter and a depth of insertion. The length of the ETT 16 is longer than the depth of insertion, and the depth of insertion is not a characteristic metric of the ETT per se. However, the depth of insertion is typically determined for a given patient prior to performing the tracheal intubation. Thus, the ETT sizing for the patient P includes sizing both the ETT diameter and the depth of insertion. That is, the ETT size as used herein includes a tube diameter (specified by an inner diameter (ID) an outer diameter (OD), or both an ID and an OD) and a depth of insertion.

Figure 2:
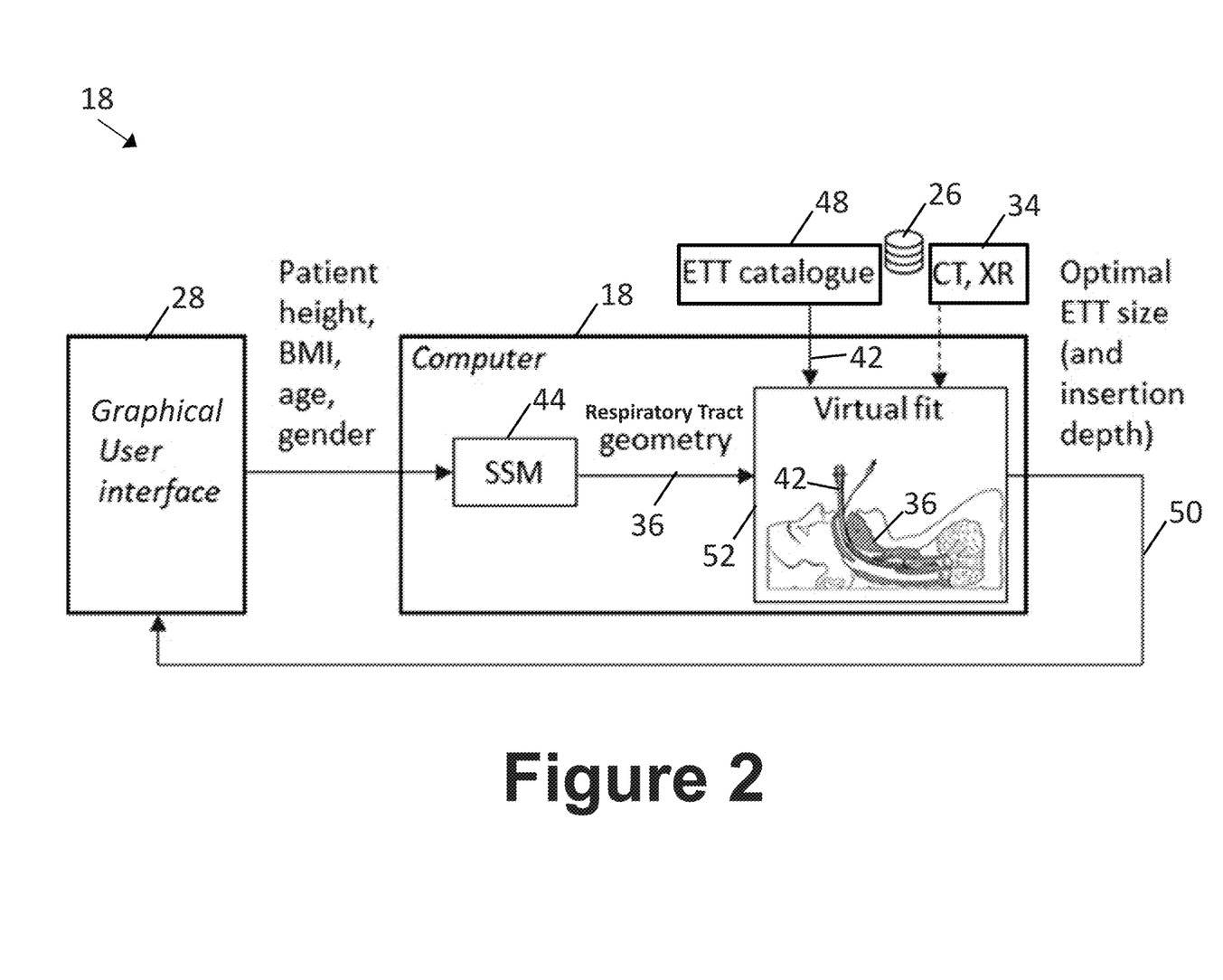
FIG. 2 diagrammatically illustrates another view of the intubation assistance device of FIG. 1.

With continuing reference to FIG. 1 and with further reference to FIG. 2, an intubation assistance device 18 configured to assist with intubation of the ETT 16 by providing a recommended ETT size (e.g., diameter and depth of insertion) prior to performing the tracheal intubation. FIG. 2 diagrammatically shows the intubation assistance device 18 in additional detail. The intubation assistance device 18 can comprise an electronic processing device, such as a workstation computer (more generally, a computer), a smart device (e.g., a smartphone, a tablet, and so forth), or server computer or a plurality of server computers, (e.g., interconnected to form a server cluster, cloud computing resource, or so forth). The intubation assistance device 18 includes typical components, such as an electronic controller 20 (e.g., an electronic processor or a microprocessor), at least one user input device (e.g., a mouse, a keyboard, a trackball, a finger swipe on a touchscreen of a smart device, and/or the like) 22, and at least one display device 24 (shown only in FIG. 1, e.g., an LCD display, plasma display, cathode ray tube display, and/or so forth). In some embodiments, the display device 24 can be a separate component from the electronic processing device 18. The display device 24 may also comprise two or more display devices.

The electronic controller 20 is operatively connected with a one or more non-transitory storage media 26. The non-transitory storage media 26 may, by way of non-limiting illustrative example, include one or more of a magnetic disk, RAID, or other magnetic storage medium; a solid state drive, flash drive, electronically erasable read-only memory (EEROM) or other electronic memory; an optical disk or other optical storage; various combinations thereof; or so forth; and may be for example a network storage, an internal hard drive of the intubation assistance device 18, various combinations thereof, or so forth. It is to be understood that any reference to a non-transitory medium or media 26 herein is to be broadly construed as encompassing a single medium or multiple media of the same or different types. Likewise, the electronic controller 20 may be embodied as a single electronic processor or as two or more electronic processors. The non-transitory storage media 26 stores instructions executable by the at least one electronic controller 20. The instructions include instructions to generate a graphical user interface (GUI) 28 for display on the remote operator display device 24.

In some embodiments, one or more cameras are disposed in an area where the medical imaging device 15 is located. For example, as shown in FIG. 1, a three-dimensional (3D) camera 30 can be positioned to image the patient P. Although only one 3D camera 30 is shown in FIG. 1, any suitable 3D camera 30 can be used.

Furthermore, as disclosed herein, the non-transitory storage media 26 stores instructions executable by the at least one electronic controller 20 to perform an intubation assistance method or process 100 determining a suitable size and/or insertion depth of the ETT 16 to be used with the mechanical ventilator 2 to provide ventilation therapy to the patient P.

It will be appreciated that, as previously noted, the mechanical ventilator 2 (and the 3D camera 30) can be disposed in a first room of a medical facility, while the image acquisition device 15 and the electronic processing device 18 can be disposed in a second, different room of the medical facility. This is depicted by the dashed line L in the generally "middle" portion of FIG. 1. In another example, the mechanical ventilator 2 and the electronic processing device 18 can be disposed in the first room, while the image acquisition device 15 is disposed in the second room of the medical facility. In a further example, each of the mechanical ventilator 2, the image acquisition device 15 and the electronic processing device 18 can be disposed in separate rooms of the medical facility. These are merely illustrative examples.

There may also be substantial temporal separation between (i) the acquisition of the images of the patient P using the imaging device 15 and determination of the ETT size recommendation for the patient P using the intubation assistance device 18, and (ii) the actual tracheal intubation of the patient P. For example, the patient P may first be transported on a gurney to a radiology lab housing the imaging device 15 for imaging and ETT sizing, and then transported on the gurney from the radiology lab to the location of the mechanical ventilator 2. In some embodiments described herein, the temporal separation may be even larger than this. For example, if the patient P undergoes a thoracic CT examination for some routine or diagnostic medical purpose, then as disclosed herein the acquired images may be used for that routine or diagnostic medical purpose and also be secondarily leveraged to generate an ETT recommendation that may be stored in the Electronic Health Record (EHR) or other medical record of the patient P. Thereafter, if at some point (possibly weeks, months, or even years later) the patient P comes under medical care and requires mechanical ventilation, the ETT recommendation can be retrieved from the EHR or other medical record of the patient P and referenced by the anesthesiologist or other qualified medical professional performing the tracheal intubation.

FIG. 1 also shows a user interface device 10, which can comprise, for example, a mobile device, Google Glass (available from Alphabet Inc., Mountain View, CA, USA), Microsoft Hololens (available from Microsoft Inc., Bellevue, WA, USA), a local computer (i.e., a workstation), a handheld tablet, a patient monitor, or the mechanical ventilator 2. In some embodiments, the user interface device 10 is used by a medical professional in a room where the mechanical ventilator 2 is disposed, while in other embodiments, the user interface device 10 is disposed in a room where the medical imaging device 15 is disposed. The user interface device 10 is diagrammatically shown as a box in FIG. 1, and is configured to receive one or more inputs from a user, and generate outputs from the inputs (e.g., a recommended ETT size 50, see FIG. 2). For example, a clinician can open an application ("app") on the user interface device 10, and input patient parameters such as gender, height, weight, and age. From these inputs, the app can output a recommended ETT size 50 for the patient P on the user interface device 10. Optionally, the inputs can be estimated and pre-filled using image processing and machine learning techniques from with images from an optical camera, and/or a lidar sensor of the user interface device 10. For this, the clinician can take a camera/lidar picture of the patient P, from which gender, height, weight, BMI, and age are automatically estimated. This could be done by drawing automatically identified landmarks (shoulder, hip, armpit, etc.) on the picture and ask the clinician to verify their position. Furthermore, the automatically suggested prefills of these numerical/categorical inputs can be overridden interactively by direct user inputs where either data is available or the prefills seem unlikely.

Figure 3:
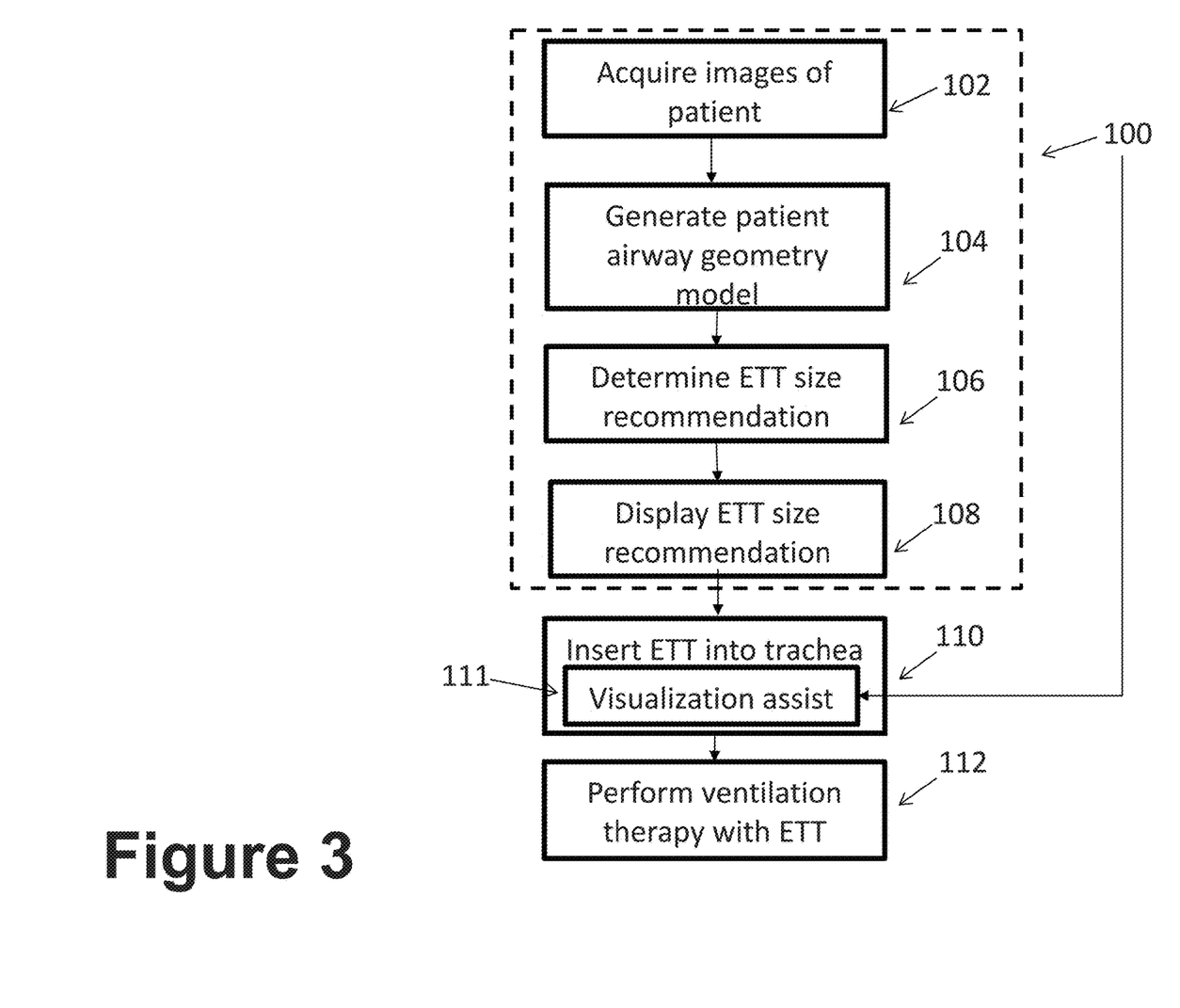
FIG. 3 shows an example flow chart of operations suitably performed by the system of FIG. 1.

With reference to FIG. 3, and with continuing reference to FIGS. 1 and 2, an illustrative embodiment of the intubation assistance method 100 is diagrammatically shown as a flowchart. At an (optional) operation 102, one or more images 34 of the patient are obtained by the medical imaging device 15. In a particular example, the acquired images 34 are CT images 34. To acquire the CT images 34, the electronic controller 20 is configured to control the medical imaging device 15 (i.e., a CT scanner) to acquire the CT images 34 of the upper airway or respiratory tract (e.g., from the nose or the mouth to the carina) of the patient P. In some embodiments, the electronic controller 20 is configured to control the medical imaging device 15 to acquire a diagnostic torso CT image of the patient P at a first X-ray level, and an extended upper CT image extending upward from the diagnostic torso CT image of the patient P at a second X-ray level that is lower than the first X-ray level. The electronic controller 20 is then configured to combine the diagnostic torso CT image and the extended upper CT image to generate the CT images 34 of the respiratory tract of the patient P. This approach of lowering the X-ray level for the extended upper CT image can be advantageous as the throat area can be sensitive to radiation damage, so that a lower X-ray level in this area provides lower dosage. Additionally, the amount of image detail required for performing the disclosed ETT sizing may be less than may be required for the diagnostic or screening task for which the torso CT examination was ordered, so that the lower X-ray level used for the extended upper CT image is sufficient for this purpose. This type of imaging sequence workflow may be particularly advantageous when performing the ETT sizing as a secondary result of a torso CT examination ordered for a specific diagnostic or screening task unrelated to ETT sizing.

In some embodiments, one or more 3D images 38 showing an exterior (i.e., head and thorax) of the patient P can be acquired. To do so, the 3D images 38 are obtained by the 3D camera(s) 30 and transmitted to the electronic processing device 18. The electronic controller 20 is then configured to register the 3D images 38 of the exterior of the patient P with the CT images 34 to obtain a hybrid imaging data set, which is used to determine the intubation pathway.

At an operation 104, information about the patient P is received (e.g., from the images 34, from data retrieved from the non-transitory computer readable media 26 of the electronic processing device 18, from data retrieved from another database such as an EHR, Electronic Medical Record (EMR) database, via one or more inputs via the user interface device 10, and so forth). The information can include one or more patient variables, such as height, weight, body-mass index, age, gender, and so forth. In some examples, additional measurements can be included, such as an armpit-hip distance or a shoulder-hip distance of the patient P.

Once acquired, the patient variable(s) are input into a statistical shape model (SSM) 44 of a human respiratory system including a model of at least a portion of the respiratory tract. The respiratory tract comprises the anatomy carrying airflow during inhalation and exhalation, and includes for example the upper airway (e.g., the oral cavity, pharynx, larynx, etc.), the nasal cavity, trachea, carina, bronchia, et cetera. Depending on the type of intubation to be performed, the model of the SSM 44 may represent all, or only some, of this anatomy. For example, an oral intubation may model the upper airway including the oral cavity but omit modeling of the nasal cavity, whereas a nasal intubation may model the nasal cavity but not the front portion of the oral cavity. The SSM 44 can be implemented on the electronic controller 20. From the input variables, the SSM 44 is configured to generate a patient respiratory tract geometry model 36 of the patient P. In one example embodiment, the SSM 44 is configured to generate the patient respiratory tract geometry model 36 further using the acquired CT images 34 (e.g., by determining a mean trachea diameter from the CT images 34) and/or the acquired 3D images 38. In another example, the SSM 44 is configured to update an already-generated patient respiratory tract geometry model 36 with the CT images 34 and/or the 3D images 38 of the exterior of the patient P. In another example, once the CT images 34 and/or the 3D images 38 of the exterior of the patient P are acquired, a value of at least one dimension of the respiratory tract of the patient P (e.g., a diameter of the trachea of the patient P, a length of the trachea of the patient P, and so forth) from the CT images 34 and/or the 3D images 38 of the exterior of the patient P. The at least one dimension in the patient respiratory tract geometry model 36 is then set to the determined value.

In another example embodiment, the SSM 44 is configured to generate the patient respiratory tract geometry model 36 further using an artificial neural network (ANN) 46 implemented in the electronic controller 20. The ANN 46 is trained on patient shape measurements (for example, BMI, height, weight, body dimensions such as armpit to hip), camera or medical images of the patient, and parameters of the ETT 16 selected or deemed suitable for use with patients associated with the patient shape measurements and images of the patient. The ANN 46 can receive, as inputs, the patient variables, and the CT images 34 and/or optionally the 3D images 38. From this, the ANN 46 can output the patient respiratory tract geometry model 36.

In another example embodiment, the SSM 44 is configured to generate the patient respiratory tract geometry model 36 further using variability ranges of the one or more patient inputs provided by the SSM 44. For example, the SSM 44 is based on multiple patients. Thus, the SSM 44 can be used to derive a mean shape of the respiratory tract of the patient P, and also geometric variabilities of the respiratory tract of the patient P. The geometric variabilities can be used to determine the patient respiratory tract geometry model 36, and also for cases including 5% and 95% percentile of a main mode of variability. This provides a user with data of the patient P and whether this data is sufficient in order to reach a desired placement of the ETT 16.

At an operation 106, a recommended ETT size 50 is selected. To do so, an ETT model 42 can be retrieved from the non-transitory computer readable media 26. The ETT model 42 can include information about the ETT 16, such as mechanical properties such as length, diameter, and deformation characteristics.

The retrieved ETT model(s) 42 can be modeled by modeling insertion into the patient respiratory tract geometry model 36 to form a virtual fit model 52, and estimating at least one fit parameter based on the virtual fit model 52. The at least one fit parameter may include at least one of a contact pressure between the estimated ETT model 42 and a wall of the trachea in the patient respiratory tract geometry model 36, a distance between the estimated ETT model 42 and the wall of the trachea, a friction value between the estimated ETT model 42 and the wall of the trachea, a tissue deformation of the wall of the trachea from contact by the estimated ETT model 42, various combinations thereof, and so forth.

In some embodiments, the recommended ETT size 50 is selected by selecting a candidate ETT model of a candidate ETT size from a catalog 48 of ETT models 42 of different ETT sizes. The catalog 48 of ETT models 42 can be stored in the non-transitory computer readable media 26 of the electronic processing device 18. The selected candidate model 42 is selected based on, for example a diameter of the trachea of the patient P (e.g., a maximum or minimum diameter) determined from the patient respiratory tract geometry model 36. The candidate ETT model 42 is assessed by modeling inserting the candidate ETT model 42 into the patient respiratory tract geometry model 36 to generate the virtual fit model 52 (e.g., a geometrical mapping model, a finite element model, a computational fluid dynamics model, a fluid-structure interaction model, and so forth) for that candidate ETT model 42. The at least one fit parameter for the candidate ETT size is then estimated based on the modeling. The recommended ETT size 50 is then selected as the candidate ETT size if the at least one fit parameter for the candidate ETT size satisfies a predetermined fit parameter criteria. For example, the fit parameter criteria can include a maximum permissible contact pressure between the ETT model 42 and a wall of the trachea in the patient respiratory tract geometry model 36, and by way of nonlimiting illustration in one embodiment the predetermined fit parameter criteria can be a maximum contact pressure of 1.0 MPa. If the modeling process then outputs a contact pressure of less than 1.0 MPa, then the ETT 16 is selected corresponding to the ETT in the candidate ETT model 42. In another example, the fit parameter criteria can include a maximum permissible gap distance between the ETT model 42 and the wall of the trachea from the patient respiratory tract geometry model 36, and in one nonlimiting illustrative embodiment the predetermined fit parameter criteria can be a maximum gap of 0.0 mm. Various combinations of such criteria can optionally be applied.

If the at least one fit parameter for the candidate ETT size does not satisfy the predetermined fit parameter criteria, then a different candidate ETT model of a different candidate ETT size is selected from the catalog 48. The modeling is then repeated until the predetermined fit parameter criteria is satisfied, at which point the recommended ETT size 50 is determined as the ETT size that satisfies the predetermined fit parameter criteria.

In some embodiments, the at least one fit parameter can further include a friction value between the estimated ETT model 42 and the wall of the trachea; a tissue deformation of the wall of the trachea from contact by the estimated ETT model 42, and so forth. The respiratory tract of the patient P, especially the upper airway tissue and vocal cords, are deformable and can be pushed aside by the ETT 16 during insertion. Additionally, friction between the ETT 16 and the airway wall can impose resistance to sliding. Friction and tissue deformation can influence how the ETT 16 deforms, which can influence the magnitude of the stresses and strains in the tissue. For example, if the tissue gives away due to the mechanical interaction with the ETT 16, the bending angle of the ETT 16 is reduced while the tissue strain will increase. Another aspect is slipping. The total static friction force on a positioned tube determined the risk of slipping. Therefore, considering tissue deformation and friction in the finite element calculations can further increase the accuracy of the simulations.

In other embodiments, the flow resistance in the tube plays a role in weaning. The tube diameter is the critical parameter. Flow simulations can estimate the impact of the inserted tube on the work of breathing. The outcome of the flow simulation weighs in the virtual fit module as an extra criterium. For example, the extra flow resistance imposed by the tube (compared to a non-intubated trachea) is not allowed to increase the work of breathing or decrease the tracheal pressure with more than 10%.

In some embodiments, the modeling can be used to select an insertion depth of the recommended ETT size 50. Put another way, the recommended ETT size 50 can include both a recommended ETT diameter and a recommended insertion depth. For example, since the center line of the trachea and the upper airway do not conform to the shape of the ETT 16, the ETT 16 may touch or contact a tracheal wall at different sides. The ETT model 42 can be used to account for a difference between the actual required depth of insertion of the ETT 16 and the length of the center line of the determined length of the intubation pathway. The ETT model 42 is virtually inserted into the patient respiratory tract geometry model 36 forming the virtual fit model 52 until the ETT model 42 is, for example, 5.0 cm above the carina in the patient respiratory tract geometry model 36.

At an operation 108, the recommended ETT size 50 for the patient P is displayed, via the GUI 28, on the display device 24 of the electronic processing device 18. Additionally or alternatively, the recommended ETT size 50 can be transmitted to the mechanical ventilator 2 for display on the display device 14 thereof, or to the user interface device 10. Advantageously, a medical professional in the room where the mechanical ventilator 2 can quickly see the recommended ETT size for the patient P on the mechanical ventilator 2.

In some embodiments, the displaying operation 108 can includes displaying a rendering on the display device 24 (or the display 14 of the mechanical ventilator 2) of the virtual fit model 52 depicting the ETT model 42 of the recommended ETT size inserted into the patient respiratory tract geometry model 36. This rendering may, for example, correspond to the rendering of the virtual fit model 52 shown in FIG. 2.

The method 100 performed by the intubation assistance device 18 is typically complete at operation 108 in which the recommended ETT size 50 is displayed. At an operation 110, the ETT 16 having the recommended ETT size 50 for the patient P is physically inserted into the trachea of the patient P in an intubation process. The medical professional can use markings conventionally included on the ETT 16 to determine progress of the insertion depth of the ETT. The ETT 16 is inserted into the trachea to the recommended depth of insertion so as to place the tip of the ETT 16 at a desired point (e.g., 5.0 cm above the carina). In some embodiments, the method 100 performed by the intubation assistance device 18 may optionally continue during the intubation process, by further include present visual assistance 111 by way of a heads-up display (HUD), such as augmented reality (AR) glasses or headset (e.g., a Microsoft HoloLens, Bellevue, WA, United States) (not shown) that can be used by the medical professional during placement (and subsequent removal) of the ETT 16. In particular, the AR device can be used to indicate the position of the ETT 16 in relation to relevant anatomical structures within the patient's body derived from the CT images 34 and/or from the head and neck model 36. For example, the visual assist 111 may monitor the visible markings on the ETT 16 to continually monitor depth of insertion, and can display the virtual fit model 52 with the ETT model 42 of the recommended ETT size 50 inserted to that depth into the patient respiratory tract geometry model 36. This further aids in improving the accuracy of positioning of the ETT 16 and thereby decrease the risk of complications.

At an operation 112, the ETT 16 is connected to the mechanical ventilator 2 (e.g., at the port or connector 8). The medical professional then operates the mechanical ventilator 2 to deliver ventilation therapy to the patient P with the mechanical ventilator 2.

Since the information can be obtained from any thorax CT image 34, the CT image acquisition and the ventilation therapy can be separated in time by days, weeks, months, or even years. For example, if a patient gets a thorax CT image 34 for some unrelated medical purpose, the recommended ETT size 50 for the patient including the ETT diameter and depth of insertion can be calculated routinely and stored in an electronic patient record (e.g., similar to a blood type of the patient). If the patient requires at any time later mechanical ventilation (e.g., after a car accident) then the information can be retrieved from the electronic patient record. This may be particularly useful since the ETT 16 may be placed by an emergency medicine technician rather than a consultant anesthetist, and often in a situation where time pressures and clinical issues (e.g., blood in the airway) may make ETT placement more difficult.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. An intubation assistance device comprising an electronic controller configured to:
generate a patient respiratory tract geometry model of at least a portion of a human respiratory tract by inputting one or more patient variables into a statistical shape model (SSM) of at least a portion of the human respiratory tract, wherein the one or more patient variables include at least one of: height, weight, body-mass index, age, and gender;
select a recommended endotracheal tube (ETT) size by modeling at least one ETT model inserted into the patient respiratory tract geometry model to form a virtual fit model and estimating at least one fit parameter based on the virtual fit model; and
display the recommended ETT size on a display device.

2. The device of claim 1, wherein the electronic controller is further configured to:
select an insertion depth of the recommended ETT based on the modeling of the at least one ETT model inserted into the patient respiratory tract geometry model.

3. The device of claim 1, wherein the electronic controller is configured to select the recommended ETT size by:
selecting a candidate ETT model of a candidate ETT size from a catalog of ETT models of different ETT sizes;
modeling the candidate ETT model inserted into the patient respiratory tract geometry model;
estimating the at least one fit parameter for the candidate ETT size based on the modeling; and
selecting the recommended ETT size as the candidate ETT size if the at least one fit parameter for the candidate ETT size satisfies a predetermined fit parameter criteria.

4. The device of claim 3, wherein the electronic controller is further configured to, if the at least one fit parameter for the candidate ETT size does not satisfy the predetermined fit parameter criteria:
select a different candidate ETT model of a different candidate ETT size from the catalog; and
repeat the modeling until the predetermined fit parameter criteria is satisfied.

5. The device of claim 1, wherein the at least one fit parameter includes at least one of: a contact pressure between the estimated ETT model and a wall of the trachea; a distance between the estimated ETT model and the wall of the trachea; a friction value between the estimated ETT model and the wall of the trachea; and/or tissue deformation of the wall of the trachea from contact by the estimated ETT model.

6. The device of claim 1, wherein the electronic controller is further configured to:
receive the one or more patient variables from an electronic processing device and/or retrieve the one or more patient variables from a patient database.

7. The device of claim 1, wherein the electronic controller is further configured to display the recommended ETT size by operations including:
displaying a rendering on the display device of the modeling the ETT model of the recommended ETT size inserted into the patient respiratory tract geometry model.

8. The device of claim 1, wherein the electronic controller is configured to generate the patient respiratory tract geometry model from variability ranges of the one or more patient inputs provided by the SSM.

9. The device of claim 1, wherein the electronic controller is further configured to:
receive one or more images of the respiratory system of the patient;
determine a value of at least one dimension of the respiratory tract of the patient from the one or more images; and
set the at least one dimension in the patient respiratory tract geometry model to the determined value.

10. The device of claim 9, further including:
an imaging device configured to acquire the one or more images.

11. The device of claim 10, wherein the imaging device is a computed tomography (CT) imaging device configured to acquire one or more CT images of the patient.

12. The device of claim 11, further including a second imaging device comprising one or more three-dimensional (3D) cameras positioned in an area where the patient is disposed, the one or more 3D cameras being configured to acquire one or more 3D images of the patient.

13. An intubation assistance method comprising, with an electronic controller:
generating a patient respiratory tract geometry model of at least a portion of a human respiratory tract by inputting one or more patient variables into a statistical shape model (SSM) of at least a portion of the human respiratory tract, wherein the one or more patient variables include at least one of: height, weight, body-mass index, age, and gender;
selecting a recommended endotracheal tube (ETT) size based on the patient respiratory tract geometry model and an estimation of at least one fit parameter; and
displaying the recommended ETT size on a display device.

14. The method of claim 13, wherein the patient respiratory tract geometry model is generated from an artificial neural network (ANN) trained on patient shape measurements, images of the patient, and parameters of an ETT.

15. The device of claim 1, wherein the one or more patient variables include at least two of: height, weight, body-mass index, age, gender, armpit-hip distance, and shoulder-hip distance.

16. The method of claim 13, wherein the one or more patient variables include at least two of: height, weight, body-mass index, age, gender, armpit-hip distance, and shoulder-hip distance.

* * * * *